(12) United States Patent
Barker et al.

(10) Patent No.: US 9,637,800 B2
(45) Date of Patent: May 2, 2017

(54) DIAGNOSTIC TEST FOR BACTERIAL PATHOGENS USING INTERNAL CONTROL BACTERIAL STRAIN

(71) Applicant: Animal Health Trust, Kentford, Newmarket, Suffolk (GB)

(72) Inventors: Colin Richard Barker, Newmarket (GB); Katy Susan Webb, Newmarket (GB); Andrew Stephen Waller, Newmarket (GB)

(73) Assignee: ANIMAL HEALTH TRUST, Kentford, Newmarket, Suffolk (GB)

( * ) Notice: Subject to any disclaimer, the term of this patent is extended or adjusted under 35 U.S.C. 154(b) by 0 days.

(21) Appl. No.: 14/367,479

(22) PCT Filed: Dec. 21, 2012

(86) PCT No.: PCT/GB2012/053235
§ 371 (c)(1),
(2) Date: Jun. 20, 2014

(87) PCT Pub. No.: WO2013/093498
PCT Pub. Date: Jun. 27, 2013

(65) Prior Publication Data
US 2015/0051082 A1 Feb. 19, 2015

(30) Foreign Application Priority Data

Dec. 22, 2011 (GB) .................................. 1122121.5

(51) Int. Cl.
*C07H 21/04* (2006.01)
*C12Q 1/68* (2006.01)

(52) U.S. Cl.
CPC ....... *C12Q 1/689* (2013.01); *C12Q 2545/101* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 6,558,901 | B1 | 5/2003 | Catanzariti et al. | |
|---|---|---|---|---|
| 2006/0166232 | A1 | 7/2006 | Vickery et al. | |
| 2010/0233720 | A1* | 9/2010 | Gayral | C12N 1/06 435/6.16 |
| 2011/0201007 | A1* | 8/2011 | Waller | C12Q 1/689 435/6.11 |

FOREIGN PATENT DOCUMENTS

| WO | WO 98/58945 A1 | 12/1998 |
|---|---|---|
| WO | WO 2007/115059 A2 | 10/2007 |
| WO | WO 2010/046648 A2 | 4/2010 |
| WO | WO 2011/099855 A1 | 8/2011 |

OTHER PUBLICATIONS

Buck et al. Biotechniques, vol. 27, pp. 528-536, Sep. 1999.*
Kolk et al. (J. of Clinical Microbiology, vol. 32, No. 5, pp. 1354-1356, 1994).*
Preziuso et al. (J. of Equine Veterinary Science, vol. 32, pp. 292-296, Dec. 14, 2011).*
Baverud et al. (Veterinary Microbiology, vol. 124, pp. 219-229, 2007).*
Alber et al., "Multiplex polymerase chain reaction for identification and differentiation of *Streptococcus equi* subsp. *zooepidemicus* and *Streptococcus equi* subsp. *equi*", J. Vet. Med. B Infect. Dis. Public Health. vol. 51, No. 10, pp. 455-458 (2004).
Artiushin et al., "Thermophilic helicase-dependent DNA amplification using the IsoAmp™ SE experimental kit for rapid detection of *Streptococcus equi* subspecies *equi* in clinical samples", J. Vet. Diag. Invest., vol. 23, No. 5, pp. 909-914 (2011).
Baverud et al., "Real-time PCR for detection and differentiation of *Streptococcus equi* subsp. *equi* and *Streptococcus equi* subsp. *zooepidemicus*", Vet. Microbiol., vol. 124, No. 3-4, pp. 219-229 (2007).
Kolk et al., "*Mycobacterium smegmatis* strain for detection of *Mycobacterium tuberculosis* by PCR used as internal control for inhibition of amplification and for quantification of bacteria", J. Clin. Microbiol., vol. 32, No. 5, pp. 1354-1356 (1994).
Newton et al., "Control of strangles outbreaks by isolation of guttural pouch carriers identified using PCR and culture of *Streptococcus equi*", Equine Vet. J. vol. 32, No. 6, pp. 515-526 (2000).

* cited by examiner

*Primary Examiner* — Jeanine A Goldberg
(74) *Attorney, Agent, or Firm* — McDermott Will & Emery LLP (57) ABSTRACT

The invention relates to a method for detecting the presence or absence of a bacterial pathogen in a biological sample obtained from a human or animal subject, using an internal control. In particular, the invention relates to a method for detecting the presence or absence of *Streptococcus equi* in an equine sample using a control bacterial strain as internal control for DNA extraction and PCR. The invention also relates to host cells (such as bacterial cells) and nucleic acids for use as internal standard in said method in addition to diagnostic kits comprising said host cells and nucleic acids.

11 Claims, 2 Drawing Sheets

SEQUENCE LISTING

<160> NUMBER OF SEQ ID NOS: 21

<210> SEQ ID NO 1
<211> LENGTH: 82
<212> TYPE: DNA
<213> ORGANISM: Artificial
<220> FEATURE:
<223> OTHER INFORMATION: Synthetic sequence

<400> SEQUENCE: 1
ccgtgtatta cgcatgcggg tagattatgt aggtagagac atccaggtca agttctcgac    60
cttctcgtgg gaggtgaacc ag                                             82

<210> SEQ ID NO 2
<211> LENGTH: 22
<212> TYPE: DNA
<213> ORGANISM: Artificial
<220> FEATURE:
<223> OTHER INFORMATION: Synthetic primer

<400> SEQUENCE: 2
cgcatgcggg tagattatgt ag                                             22

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
tcccacgaga aggtcgagaa                                                20

<210> SEQ ID NO 4
<211> LENGTH: 17
<212> TYPE: DNA
<213> ORGANISM: Artificial
<220> FEATURE:
<223> OTHER INFORMATION: Synthetic probe

<400> SEQUENCE: 4
agagacatcc aggtcaa                                                   17

<210> SEQ ID NO 5
<211> LENGTH: 22
<212> TYPE: DNA
<213> ORGANISM: Artificial
<220> FEATURE:
<223> OTHER INFORMATION: Synthetic primer

<400> SEQUENCE: 5
ccgaatttgt ccaagtggta tg                                             22

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
gcactccgtt atactcactg                                                20

<210> SEQ ID NO 7
<211> LENGTH: 20

```
<212> TYPE: DNA
<213> ORGANISM: Artificial
<220> FEATURE:
<223> OTHER INFORMATION: Synthetic primer

<400> SEQUENCE: 7
tttgctagtg ctactcctgc                                         20

<210> SEQ ID NO 8
<211> LENGTH: 19
<212> TYPE: DNA
<213> ORGANISM: Artificial
<220> FEATURE:
<223> OTHER INFORMATION: Synthetic primer

<400> SEQUENCE: 8
atgggaacag gactacttg                                          19

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
gtcttagctt cctctttcgc                                         20

<210> SEQ ID NO 10
<211> LENGTH: 32
<212> TYPE: DNA
<213> ORGANISM: Artificial
<220> FEATURE:
<223> OTHER INFORMATION: Synthetic primer

<400> SEQUENCE: 10
gacgacgaat tctgagaggc aagtgacgag tc                           32

<210> SEQ ID NO 11
<211> LENGTH: 44
<212> TYPE: DNA
<213> ORGANISM: Artificial
<220> FEATURE:
<223> OTHER INFORMATION: Synthetic primer

<400> SEQUENCE: 11
gacgaccgat cggacgacac cggtttgcca aactcccttc caag              44

<210> SEQ ID NO 12
<211> LENGTH: 33
<212> TYPE: DNA
<213> ORGANISM: Artificial
<220> FEATURE:
<223> OTHER INFORMATION: Synthetic primer

<400> SEQUENCE: 12
gacgaccgat cgcacttgct tgttctagct gag                          33

<210> SEQ ID NO 13
<211> LENGTH: 32
<212> TYPE: DNA
<213> ORGANISM: Artificial
<220> FEATURE:
<223> OTHER INFORMATION: Synthetic primer

<400> SEQUENCE: 13
```
gacgacgtcg acggaacgaa cctcttacca ca                32

<210> SEQ ID NO 14
<211> LENGTH: 24
<212> TYPE: DNA
<213> ORGANISM: Artificial
<220> FEATURE:
<223> OTHER INFORMATION: Synthetic primer

<400> SEQUENCE: 14
ttggaaagtt acacgttact aaag                         24

<210> SEQ ID NO 15
<211> LENGTH: 21
<212> TYPE: DNA
<213> ORGANISM: Artificial
<220> FEATURE:
<223> OTHER INFORMATION: Synthetic primer

<400> SEQUENCE: 15
gggcgaattg gggtaccggg c                            21

<210> SEQ ID NO 16
<211> LENGTH: 20
<212> TYPE: DNA
<213> ORGANISM: Artificial
<220> FEATURE:
<223> OTHER INFORMATION: Synthetic primer

<400> SEQUENCE: 16
tgggattctg tgccgatttt                              20

<210> SEQ ID NO 17
<211> LENGTH: 24
<212> TYPE: DNA
<213> ORGANISM: Artificial
<220> FEATURE:
<223> OTHER INFORMATION: Synthetic primer

<400> SEQUENCE: 17
ccctgaaagc atcacaattc taaa                         24

<210> SEQ ID NO 18
<211> LENGTH: 24
<212> TYPE: DNA
<213> ORGANISM: Artificial
<220> FEATURE:
<223> OTHER INFORMATION: Synthetic primer

<400> SEQUENCE: 18
caacgcgtag aagaacgatc taaa                         24

<210> SEQ ID NO 19
<211> LENGTH: 22
<212> TYPE: DNA
<213> ORGANISM: Artificial
<220> FEATURE:
<223> OTHER INFORMATION: Synthetic primer

<400> SEQUENCE: 19
cctccaattg agcttttggg tt                           22

<210> SEQ ID NO 20
<211> LENGTH: 21
<212> TYPE: DNA
<213> ORGANISM: Artificial

```
<220> FEATURE:
<223> OTHER INFORMATION: Synthetic probe

<400> SEQUENCE: 20
attgttacta tggctgaagg t                                                   21

<210> SEQ ID NO 21
<211> LENGTH: 17
<212> TYPE: DNA
<213> ORGANISM: Artificial
<220> FEATURE:
<223> OTHER INFORMATION: Synthetic probe

<400> SEQUENCE: 21
aagccaagga agccact                                                        17
```

DIAGNOSTIC TEST FOR BACTERIAL PATHOGENS USING INTERNAL CONTROL BACTERIAL STRAIN

CROSS-REFERENCE TO RELATED APPLICATIONS

This application is a U.S. National Stage of International Patent Application No. PCT/GB2012/053235, filed Dec. 21, 2012, which claims the benefit of priority to GB Application No. 1122121.5, filed Dec. 22, 2011, each of which is hereby incorporated by reference in its entirety.

REFERENCE TO A SEQUENCE LISTING

A Sequence Listing is submitted with this application in the form of a text file, created Jun. 17, 2014, and titled "0917430013seq.txt" (4,303 bytes), the contents of which are incorporated herein by reference in their entirety.

FIELD OF THE INVENTION

The invention relates to a method for detecting the presence or absence of a bacterial pathogen in a biological sample obtained from a human or animal subject. In particular, the invention relates to a method for detecting the presence or absence of *Streptococcus equi* in an equine sample. The invention also relates to host cells and nucleic acids for use in said method in addition to diagnostic kits comprising said host cells and nucleic acids.

BACKGROUND OF THE INVENTION

*Streptococcus* is a genus of spherical shaped Gram-positive bacteria. Clinically, individual species of *streptococci* are classified primarily based on their Lancefield serotyping—according to specific carbohydrates in the bacterial cell wall. These are named Lancefield groups A to T. However the pathogens in these different groups share many similarities at the genetic level. For example *Streptococcus equi* (which is in group C1 and which is the causative agent of equine strangles) shares 80% genome identity with the human pathogen *S. pyogenes* (which is in group A, and which is the causative agent of many human conditions including strep throat, acute rheumatic fever, scarlet fever, acute glomerulonephritis and necrotizing fasciitis). Additionally the two organisms share many near identical toxins and virulence factors. *Streptococci* are further characterised via their haemolytic properties. Alpha haemolysis is caused by a reduction of iron in haemoglobin giving it a greenish color on blood agar. Beta only haemolysis is complete rupture of red blood cells giving distinct, wide, clear areas around bacterial colonies on blood agar. Other *streptococci* are labeled as gamma haemolytic.

Strangles, caused by *Streptococcus equi* subspecies *equi* (*S. equi*), is the most frequently diagnosed infectious disease of horses worldwide and is responsible for significant welfare cost and economic losses to the equine industry. The disease is characterised by abscessation of the lymph nodes of the head and neck. Abscesses formed in the retropharyngeal lymph nodes usually rupture into the guttural pouches, which drain via the nostrils leading to the classical mucopurulent nasal discharge associated with strangles. However, the purulent material in a proportion of guttural pouches fails to drain completely. Over time this becomes inspissated, enabling live *S. equi* to persist in horses that have recovered from the acute disease for up to several years in the absence of obvious clinical signs (Newton et al., 1997). *S. equi* periodically sheds from persistently infected carrier horses allowing transmission to naïve individuals and resulting in new outbreaks of disease. The generation and persistence of carriers within equine populations is proposed to have been critical to the global spread of *S. equi* infection and the efficient identification and treatment of carriers is key to the prevention and eradication of this important disease.

Traditionally the diagnosis of *S. equi* infection was based upon the culture of this β-haemolytic organism using selective media, followed by biochemical tests, which rely on the inability of *S. equi* to ferment lactose, sorbitol or ribose (Bannister et al., 1985). The isolation of β-haemolytic colonies is complicated by the presence of other bacteria most notably the closely related opportunistic pathogen *Streptococcus equi* subspecies *zooepidemicus* (*S. zooepidemicus*). This β-haemolytic organism confounds the isolation of *S. equi* leading to the generation of potential false-negative results. Furthermore, as the culture test identifies *S. equi* through a lack of sugar fermentation, strains of *S. zooepidemicus* that also fail to ferment these sugars (Holden et al., 2009) can be mis-identified as *S. equi* leading to the reporting of false-positive results. Finally, the isolation and identification of *S. equi* is time consuming and requires a minimum of 48 hours from receipt of clinical samples. This reporting delay often has consequences for the isolation of infected horses providing *S. equi* with greater opportunity to transmit through the horse population.

Advances in nucleic acid based technologies and the increased number of published pathogen genome sequences has had a significant impact on the diagnosis of infectious diseases. The first PCR-based test developed for *S. equi* targeted the 5' region of the SeM gene, which encodes a cell wall anchored protein, thought to be important in the virulence of *S. equi*. Using this target, up to 3 times more clinical samples were positive for *S. equi* than by culture and biochemical tests alone (Newton et al., 2000; Timoney and Artiushin, 1997).

Historically, the SeM gene was thought to be non-variant based upon its HindIII restriction pattern on Southern blotting (Galan and Timoney, 1988). However, this has since been disproved in a number of separate studies that have demonstrated that not only is this region of the SeM gene highly variable (Anzai et al., 2005; Kelly et al., 2006), with 99 alleles identified to date (http:/pubmlst.org/perl/mlstdb-net/agdbnet.pl?file=sz_seM.xml, last accessed Nov. 12, 2011), but that it is also frequently deleted in strains of *S. equi* isolated from persistently infected carriers (Chanter et al., 2000). These results highlight that SeM should no longer be considered a suitable PCR target for the diagnosis of *S. equi* infection as sequence variation in primer binding sites and loss of the target may lead to the reporting of false-negative results.

The loss of diagnostic PCR targets leading to incorrect reporting can have serious consequences for the control of infectious disease. In Sweden, the occurrence of a 377 bp deletion in CDS1 of the pSW2 plasmid of the human pathogen *Chlamydia trachomatis* resulted in the false-negative diagnosis of many infected patients, and the rapid spread of this variant within the population, to the extent that in Sweden the variant accounted for 20-64% of current infections (Seth-Smith et al., 2009). The completion of the *S. equi* strain 4047 (Se4047) and *S. zooepidemicus* strain H70 (SzH70) genome sequences (Holden et al., 2009) has enabled the identification of alternative *S. equi*-specific targets suitable for multiplex diagnostic PCR-based tests, that reduce the risk of false-negative reporting.

A multiplex assay based upon a region of the superoxide dismutase gene (sodA) present in both *S. equi* sub-species and the *S. equi*-specific gene seeI was developed to identify and differentiate *S. equi* and *S. zooepidemicus* isolated on culture plates (Baverud et al., 2007). However, the ability of this test to identify *S. equi* direct from clinical sample material was not determined.

There is therefore a need to provide a robust and sensitive diagnostic test for horses infected with *S. equi* and in particular overcome the problems with conventional methodology primarily related to the existence of false-negative results.

SUMMARY OF THE INVENTION

According to a first aspect of the invention, there is provided a method for detecting the presence or absence of a bacterial pathogen in a biological sample, the method comprising the steps of:
(a) adding a control bacterial strain to a biological sample obtained from a human or animal subject, wherein the genome of the control bacterial strain contains a target sequence region which differs from a sequence within the bacterial pathogen;
(b) assessing the sample for the presence or absence of one or more genes specific for the bacterial pathogen, wherein positive identification of the one or more genes specific for the bacterial pathogen is indicative of a positive identification for the bacterial pathogen in the biological sample; and
(c) assessing the sample for the presence of the target sequence region within the control bacterial strain, wherein positive identification of the target sequence region within the control bacteria is indicative of an accurate result for step (b).

According to a further aspect of the invention there is provided a nucleic acid sequence comprising SEQ ID NO: 1.

According to a further aspect of the invention, there is provided a control bacterial strain (i.e. host cell) comprising a vector which comprises the nucleic acid of SEQ ID NO: 1.

According to a further aspect of the invention there is provided a diagnostic kit for detecting the presence or absence of a bacterial pathogen, such as *S. equi*, which comprises:
(a) a vector which contains a target sequence region which differs from the sequence of the bacterial pathogen; and
(b) primers and/or probes directed to the target sequence region and one or more genes specific for the bacterial pathogen.

DETAILED DESCRIPTION OF THE INVENTION

According to a first aspect of the invention, there is provided a method for detecting the presence or absence of a bacterial pathogen in a biological sample, the method comprising the steps of:
(a) adding a control bacterial strain to a biological sample obtained from a human or animal subject, wherein the genome of the control bacterial strain contains a target sequence region which differs from a sequence within the bacterial pathogen;
(b) assessing the sample for the presence or absence of one or more genes specific for the bacterial pathogen, wherein positive identification of the one or more genes specific for the bacterial pathogen is indicative of a positive identification for the bacterial pathogen in the biological sample; and
(c) assessing the sample for the presence of the target sequence region within the control bacterial strain, wherein positive identification of the target sequence region within the control bacteria is indicative of an accurate result for step (b).

Although it will be appreciated that the inventive methodology may equally apply to any bacterial pathogen (such as *Mycobacterium tuberculosis, Streptococcus, Pseudomonas, Shigella, Campylobacter* and *Salmonella*) which is intended to be detected, the invention finds particular utility in the detection of *Streptococcus*, such as *Streptococcus equi*. Therefore, in one embodiment, the bacterial pathogen is *Streptococcus equi*.

As discussed hereinbefore, the existing methodology for detecting the presence of *Streptococcus equi* has the disadvantage of providing false-negative results. For example, if the diagnostic assay returns a negative result it confirms one of two results, i.e. the sample either lacks *Streptococcus equi* or there is an error with the diagnostic assay and it has not been conducted successfully.

The methodology of the present invention mixes a control bacterial strain into the sample obtained from the subject and by conducting a multiplex assay to detect sequences present within the target *Streptococcus equi* strain and the control bacterial strain, this provides a positive internal control that the multiplex assay has been successful. Surprisingly efficient results have been obtained by using the method of the invention. In particular, data is presented herein which demonstrates that the method of the invention has a limit of detection of 20 copies of *S. equi* DNA and has an overall sensitivity and specificity of 92.3% and 97.7%, respectively (as can be demonstrated in Table 1).

TABLE 1

Comparison of triplex qPCR assay of the invention with a conventional eqbE singlex qPCR test as described in WO 2010/046648

|  |  | triplex | | |
|---|---|---|---|---|
|  |  | positive | negative | total |
| eqbE singlex | positive | 12 | 2 | 14 |
|  | negative | 1 | 85 | 86 |
|  | total | 13 | 87 | 100 |

It will be appreciated that the control bacterial strain will be one which should not cross-react with any other bacteria which may exist in the biological sample. In one embodiment, the control bacterial strain is a Gram positive bacteria. In a further embodiment, the control bacterial strain is a Gram positive cocci bacteria. Examples of such Gram positive cocci include *Diplococci, Streptococcus Sarcina* or *Staphylococcus*. In one embodiment, the control bacterial strain is a *Streptococcus* strain, such as a *Streptococcus* strain other than *S. equi*. In a further embodiment, the control bacterial strain is *Streptococcus zooepidemicus*.

It will be appreciated that the most desirable manner in which to select a control bacterial strain wherein the genome contains a target sequence region which differs from a sequence within *Streptococcus equi* is to provide a control bacterial strain transformed with a target sequence which has no homology with any nucleotide sequences in the NCBI database. This would ensure that probes directed to the target sequence can be confirmed to bind to the control bacterial strain only and serve as an accurate positive internal control for the diagnostic assay. Thus, in one embodiment, the target sequence region within the control bacterial strain has no homology with any known nucleotide sequences. It will also be appreciated that the target sequence region should be flanked with restriction enzyme sites to facilitate cloning into a plasmid and subsequent transformation into the control bacterial strain. In a further embodiment, the target sequence region comprises a nucleotide sequence of:

```
                                        (SEQ ID NO: 1)
5'-CCGTGTATTACGCATGCGGGTAGATTATGTAGGTAGAGACATCCAG

GTCAAGTTCTCGACCTTCTCGTGGGAGGTGAACCAG-3'
```

The nucleotide sequence of SEQ ID NO: 1 is referred to herein as SZIC (for *Streptococcus zooepidemicus* internal control) and contains a sequence which corresponds to a forward primer (SZIC Forward: CGCATGCGGGTAGATTATGTAG; SEQ ID NO: 2), a sequence which corresponds to a reverse primer (SZIC Reverse: TCCCACGAGAAGGTCGAGAA; SEQ ID NO: 3) and a specific target sequence for the detection probe (SZIC Probe: AGAGACATCCAGGTCAA; SEQ ID NO: 4). The person skilled in the art of molecular biology techniques will understand that the sequence of SEQ ID NO: 1 can be detected by PCR using the SZIC Forward and Reverse primers or a taqman assay using the SZIC Forward and Reverse primers in combination with the SZIC Probe.

It will be appreciated that the target sequence region of SEQ ID NO: 1 constitutes an entirely novel sequence which has no homology with any sequences within the NCBI database and therefore constitutes one particular aspect of the invention. Therefore, according to a further aspect of the invention there is provided a nucleic acid sequence comprising SEQ ID NO: 1.

According to a further aspect of the invention, there is provided a vector comprising the nucleic acid comprising SEQ ID NO: 1. It will be appreciated that the vector may be any suitable moiety, such as a plasmid, suitable for transforming the control bacterial strain and integration into a chromosome of the host control bacterial strain.

The person skilled in the art of molecular biology techniques will understand how to integrate a novel target sequence region, such as the sequence of SEQ ID NO: 1 into a chromosome of the host control bacterial strain. However, for the avoidance of doubt such a process may typically involve selecting a chosen gene within the control bacterial strain. For example, where the control bacterial strain is *Streptococcus zooepidemicus*, the chosen gene may be the SZO07770 pseudogene. In this example (which is also described in more detail in the Methods section herein), selected fragments (i.e. 500 bp fragments) of the SZO07770 pseudogene may be amplified by PCR. The resultant product will suitably be designed to contain restriction enzyme sites complementary to both the chosen plasmid and the target sequence region (i.e. the sequence of SEQ ID NO: 1). The amplified products are then digested using the restriction enzyme sites which are complementary to an insertion point of a chosen plasmid (i.e. pGhost9). The digested PCR product is then ligated into the plasmid which consequently generates a plasmid containing the chosen gene (i.e. pGHost9ΔSZO07770).

The target sequence region (i.e. the sequence of SEQ ID NO: 1) is then subcloned into the generated plasmid by using the restriction enzyme sites which are complementary to the generated plasmid. In the examples described herein, the resultant plasmid (i.e. pGHost9SZIC) contains SZIC flanked by approximately 500 bp SZO07770 gene fragments.

The resultant plasmid is then transformed into the control bacterial strain (i.e. *Streptococcus zooepidemicus*, such as *Streptococcus zooepidemicus* H70) in accordance with standard techniques.

The target sequence region (i.e. SZIC) must then be integrated into the chromosomal copy of the selected gene (i.e. SZO07770) within the control bacterial cell (i.e. *Streptococcus zooepidemicus* H70) and the plasmid must be excised. Such integration steps may be achieved in accordance with known allelic replacement mutagenesis procedures such as those described previously for constructing a ΔprtM mutant.

According to a further aspect of the invention, there is provided a control bacterial strain (i.e. host cell) comprising a vector which comprises the nucleic acid of SEQ ID NO: 1. In one embodiment the host cell is *Streptococcus zooepidemicus*, such as *Streptococcus zooepidemicus* H70.

Examples of animal subjects include horses, pigs, cattle or dogs. It will be appreciated that the method of the invention finds great utility in detecting the presence of a bacterial pathogen (i.e. *Streptococcus equi*) in an equine, such as a horse, donkey or mule. Camelids (or canines) may also be sampled since they may also harbour *S. equi*.

The sample will generally be obtained from an individual animal which is believed to be affected by or a carrier of strangles, or being at risk of these things. For example it may be obtained from symptomatic or asymptomatic, contagious or shedding horses. Examples of suitable biological samples include whole blood, blood serum, plasma, urine, saliva, or other bodily fluid, or an extract or purification therefrom, or dilution thereof.

In one embodiment, the method of the invention additionally comprises the step of extracting nucleic acid from the biological sample obtained from the human or animal subject.

Nucleic acid containing samples may be obtained from nasal swabs or washes, pus from an abscess and lavages of the guttural pouch, the primary site for asymptomatic carriage (Newton et al, 2000).

The samples may be pooled from herds or other collections. Different samples may be taken at different time e.g. 0, 7 and 14 days. The DNA sample analysed may be all or part of the sample being obtained. Alternatively, the assessment of the invention may be performed or based on an historical DNA sample, or information already obtained therefrom.

When the bacterial pathogen comprises *Streptococcus equi*, the assay methodology of step (b) of the invention may be conducted in accordance with the experimental details described in WO 2010/046648 and those described herein.

In one aspect, establishing the presence or absence of the one or more genes in step (b) and detecting the presence of the target sequence region in step (c) is performed by means of a sequence-specific probe. The detection probe will be complementary to a sequence that is present within the one or more genes. Hybridization is carried out under conditions such that the probe binds to the one or more genes to form a stable hybrid duplex only if the hybridizing regions of the probe is complementary to the nucleic acid in the sample.

In one aspect, establishing the presence or absence of the one or more genes is performed by means of a nucleic acid amplification reaction to amplify all or part of the one or more genes that may be present in the sample. The amplification reaction may be performed at the "point-of-care" using methods published in the art. For example US 2009/0215050 describes the use of solid silicon supports for detecting bacterial infection from blood or nasal swabs. A number of detection methods are described therein including fluorometric, chemiluminescent, and electrochemical methods. Other systems are described in the literature including Wang et al. (2009) Talanta Volume 78, Issue 3, pages 647-652. This relates to a biosensor having single-stranded DNA (ssDNA) probe functionalized aluminum anodized oxide (AAO) nanopore membranes useful for bacterial pathogen detection.

In one embodiment, the nucleic acid amplification reaction is performed by means of two DNA primers to amplify all or part of the one or more genes. In one embodiment, the one or more genes are detected using PCR to amplify all or part of the one or more genes that may be present in the sample. Alternatively, the PCR may be real time PCR where detecting and identifying amplified nucleic acid is achieved by hybridization with one or more sequence-specific oligonucleotide probes.

In one embodiment, the assessing step (b) comprises detecting the *Streptococcus equi* (eqbE) gene disclosed in WO 2010/046648 as SEQ ID NO: 2. Detection of the eqbE gene is described in WO 2010/046648 and herein and typically comprises the primers and probes of SEQ ID NOS: 16, 17 and 20.

In one embodiment, the assessing step (b) comprises detecting one additional gene specific for the bacterial pathogen. In a further embodiment, the additional gene assessed in step (b) comprises the SEQ 2190 gene. Detection of the SEQ 2190 gene is described herein and typically comprises the primers and probes of SEQ ID NOS: 18, 19 and 21.

The use of real time PCR system has the advantage of providing high specificity and high sensitivity (the primers and probe of the invention could detect as little as 20 copies of *Streptococcus equi* DNA by real-time PCR assay).

In one embodiment, the probes or primers may be labelled.

Where the term "label" or "labelled" is used herein this refers to a detectable molecule which is incorporated indirectly or directly into an oligonucleotide, wherein the label molecule facilitates the detection of the oligonucleotide. Methods of producing labelled probes or primers are well known to those skilled on the art (See for example, Molecular Cloning, a laboratory manual: editors Sambrook, Fritsch, Maniatis; Cold Spring Harbor Laboratory Press, 1989; Bio-Techniques "Producing single-stranded DNA probes with the Taq DNA polymerase: a high yield protocol," 10:36, 1991). Alternatively, the detectable moiety may be incorporated directly or indirectly such as, for example, by biotinylating the 5' amino group of the oligonucleotide with sulfo-NHS-biotin. Other label molecules, known to those skilled in the art as being useful for detection, include radioactively, fluorescently, enzymatically or electrochemically labelled molecules.

Various fluorescent molecules are known in the art which are suitable for use to label a nucleic acid substrate for the method of the invention. Fluorescent molecules used as labels may include amine-reactive molecules which are reactive to end terminal amines of the substrate; sulfonyl chlorides which are conjugated to the substrate through amine residues; and the like. Depending on the fluorescent molecule used, incorporating the substrate with the fluorescent molecule label includes attachment by covalent or non-covalent means. The protocol for such incorporation may vary depending upon the fluorescent molecule used. Such protocols are known in the art for the respective fluorescent molecule.

Examples of suitable labels include FAM, VIC and NED.

Probing

The method of assessment of steps (b) and (c) may comprise directly determining the binding of an oligonucleotide probe to the nucleic acid sample.

The probe may comprise a nucleic acid sequence which hybridizes specifically to a distinctive part of the one or more genes and the target sequence region.

The term "hybridization" refers to the formation of a duplex structure by two single-stranded nucleic acids due to complementary base pairing. Hybridization can occur between complementary nucleic acid strands or between nucleic acid strands that contain minor regions of mismatch. Conditions under which only fully complementary nucleic acid strands will hybridize are referred to as "stringent hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and composition of the oligonucleotides, ionic strength, and incidence and type of mismatched base pairs.

Where the nucleic acid is double-stranded DNA, hybridisation will generally be preceded by denaturation to produce single-stranded DNA. A screening procedure, chosen from the many available to those skilled in the art, is used to identify successful hybridisation events and isolated hybridised nucleic acid. Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. Binding of a probe to target nucleic acid (e.g. DNA) may be measured using any of a variety of techniques at the disposal of those skilled in the art. For instance, probes may be radioactively, fluorescently, enzymatically or electrochemically labelled as described above.

The term "probe" refers to an oligonucleotide which forms a duplex structure with a sequence of a target nucleic acid due to complementary base pairing. The probe will consist of a "hybridizing region", which is a region of the oligonucleotide preferably consisting of 10 to 50 nucleotides, more preferably from 15 to 30 nucleotides, corresponding to a region of the target sequence.

"Corresponding" means identical to or complementary to the designated nucleic acid. An oligonucleotide probe optionally can be bound to additional molecules which allow for the detection or immobilization of the probe but do not alter the hybridization characteristics of the probe. One of skill in the art will recognize that, in general, the complement of an oligonucleotide probe is also suitable as a probe. In one embodiment, the lengths of these probes are at least 15 to 30 nucleotides. After incubation, all non-annealed nucleic acids are removed from the nucleic acid:gene hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

As discussed above, suitable probes may comprise all or part of the one or more genes in step (b) or target sequence region in step (c) (or reverse complement thereof).

Those skilled in the art are well able to employ suitable conditions of the desired stringency for selective hybridisation, taking into account factors such as oligonucleotide length and base composition, temperature and so on. Suitable selective hybridisation conditions for oligonucleotides of 17 to 30 bases include hybridization overnight at 42° C. in 6×SSC and washing in 6×SSC at a series of increasing temperatures from 42° C. to 65° C. One common formula for calculating the stringency conditions required to achieve hybridization between nucleic acid molecules of a specified sequence homology is (Sambrook et al., 1989): $T_m=81.5°$ C.+16.6 Log $[Na^+]$+0.41 (% G+C)−0.63 (% formamide)−600/#bp in duplex.

Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

Amplification-Based Methods

Preferred detection methods of the invention are based on PCR or other amplification procedures wherein all or part of the one or more genes of step (b) (if present) and the target sequence region of step (c) is amplified. The existence (and preferably identity) of any amplification product may then be assessed by any suitable method, e.g., as described herein. An example of such a method is a combination of PCR and low stringency hybridisation with a suitable probe. Unless stated otherwise, the methods of assessing the presence of the one or more genes of step (b) and the target sequence region of step (c) described herein may be performed on a native DNA sample, or on an amplification product thereof.

Where the method involves PCR, or other amplification procedure, any suitable primers designed to amplify the one or more genes of step (b) and the target sequence region of step (c) may be used. Preferably the primers both bind within the one or more genes of step (b) and the target sequence region of step (c), though one or both may flank the one or more genes of step (b) and the target sequence region of step (c), provided some or all of the one or more genes of step (b) and the target sequence region of step (c) is amplified.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. An oligonucleotide primer for use in nucleic acid amplification may be about 30 or fewer nucleotides. Generally specific primers are upwards of 14 nucleotides in length, but are preferably 15-35 inclusive, more preferably 18-32, more preferably 20-30. Those skilled in the art are well versed in the design of primers for use processes such as PCR. Various techniques for synthesizing oligonucleotide primers are well known in the art, including phosphotriester and phosphodiester synthesis methods.

Preferably the amplified region (including some of the one or more genes of step (b) and the target sequence region of step (c)) which the primers flank is less than 600, 500, 400, 300 nucleotides, more preferably less than 250 nucleotides, more preferably 20 to 200, or 50 to 180, or 100 to 150 nucleotides in length.

Suitable polymerase chain reaction (PCR) methods are reviewed, for instance, in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252: 1643-1650, (1991)). PCR comprises steps of denaturation of template nucleic acid (if double-stranded), annealing of primer to target, and polymerisation.

An amplification method may be a method other than PCR. Such methods include strand displacement activation, the QB replicase system, the repair chain reaction, the ligase chain reaction, rolling circle amplification and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic amplification reaction available in the art. As noted above, this includes (without limitation) so called "point of care" amplification reactions. Examples of results from the real time PCR genotyping assay are shown below.

Sequencing

The presence of the one or more genes of step (b) and the target sequence region of step (c) may be assessed or confirmed by nucleotide sequencing of a nucleic acid sample to determine whether all that sequence, or a characteristic portion, is present.

Nucleotide sequence analysis may be performed on a genomic DNA sample, or amplified part thereof, or RNA sample as appropriate, using methods which are standard in the art. Example sequence primers are described herein. Other techniques which may be used are single base extension techniques and pyrosequencing.

Kits

The control bacterial strain and nucleic acids disclosed herein for use in the methods of the present invention, such as an oligonucleotide probe and/or pair of amplification primers useful for the amplification of all or part of the one or more genes of step (b) and the target sequence region of step (c), and specific detection thereof, may be provided in isolated form and may be part of a kit, e.g. in a suitable container such as a vial in which the contents are protected from the external environment. The kit may include instructions for use of the nucleic acid, e.g. in PCR and/or a method for determining the presence of nucleic acid of interest in a test sample and/or in the detection of *S. equi*. Primers "substantially complementary" to these are also included. As known to those skilled in the art, a very high degree of complementarity is needed for specificity and sensitivity involving hybridization, although it need not be 100%. Thus, for example, an oligonucleotide which is identical in nucleotide sequence to an oligonucleotide disclosed herein, except for one base change or substitution, may function equivalently to the disclosed oligonucleotides. A kit wherein the nucleic acid is intended for use in PCR may include one or more other reagents required for the reaction, such as polymerase, nucleotides, buffer solution etc. A kit for use in determining the presence or absence of nucleic acid of interest may include one or more articles and/or reagents for performance of the method, such as means for providing the test sample itself, e.g. a nasal swab (such components generally being sterile).

Thus, according to a further aspect of the invention there is provided a diagnostic kit for detecting the presence or absence of a bacterial pathogen, such as *S. equi*, which comprises:

(a) a vector which contains a target sequence region which differs from the sequence of the bacterial pathogen; and (b) primers and/or probes directed to the target sequence region and one or more genes specific for the bacterial pathogen.

In one embodiment, the vector comprises the nucleic acid of SEQ ID NO: 1. In one embodiment the vector may be provided within a host cell. In a further embodiment, the host cell is *Streptococcus zooepidemicus*, such as *Streptococcus zooepidemicus* H70.

In one embodiment, the primers and/or probes directed to the target sequence region may be selected from any of the primers and probes of SEQ ID NOS: 2, 3 and 4.

In one embodiment, the primers and/or probes directed to the one or more genes specific for the bacterial pathogen, such as *S. equi*, may be selected from any of the primers and probes of SEQ ID NOS: 16, 17, 18, 19, 20 and 21.

The following studies illustrate the invention.

MATERIALS AND METHODS

Bacterial Strains, Media and Growth Conditions

Se4047 was obtained from a submandibular lymph node abscess of a New Forest pony in 1990 and SzH70 was obtained from a Thoroughbred horse in 2000 in Newmarket, England. Strains were cultured in Todd Hewett broth (Oxoid) at 37° C. with 5% $CO_2$.

Identification of Targets in *S. equi*

The selection of *S. equi* specific targets for this assay was informed by comparative genome analysis of the published Se4047 and SzH70 genomes (Heather et al., 2008; Holden et al., 2009).

Target Conservation

The eqbE and SEQ2190 target genes were PCR amplified from a DNA library of a diverse collection of 26 *S. equi* strains using the primers ZM435 and ZM436 and 2190A and 2190B, respectively (Table 2) and sequenced on an ABI3100 DNA sequencer with BigDye fluorescent terminators and the same primers used for PCR and primer ZM437 for eqbE.

TABLE 2

Primer and Probe Sequences

| Primer/probe name | Sequence | SEQ ID NO |
|---|---|---|
| ZM435 | 5'-CCGAATTTGTCCAAGTGGTATG-3' | 5 |
| ZM436 | 5'-GCACTCCGTTATACTCACTG-3' | 6 |
| ZM437 | 5'-TTTGCTAGTGCTACTCCTGC-3' | 7 |
| 2190A | 5'-ATGGGAACAGGACTACTTG-3' | 8 |
| 2190B | 5'-GTCTTAGCTTCCTCTTTCGC-3' | 9 |
| Ec07770Fwd1 | 5'-GACGACGAATTCTGAGAGGCAAGTGACGAGTC-3' | 10 |
| Ec07770Rev1a | 5'-GACGACCGATCGGACGACACCGGTTTGCCAAACTCCCTTCCAAG-3' | 11 |
| Ec07770Fwd2 | 5'-GACGACCGATCGCACTTGCTTGTTCTAGCTGAG-3' | 12 |
| Ec07770Rev2 | 5'-GACGACGTCGACGGAACGAACCTCTTACCACA-3' | 13 |
| 5' pGhost9 | 5'-TTGGAAAGTTACACGTTACTAAAG-3' | 14 |
| 3' pGhost9 | 5'-GGGCGAATTGGGGTACCGGGC-3' | 15 |
| eqbE2 forward | 5'-TGGGATTCTGTGCCGATTTT-3' | 16 |
| eqbE2 reverse | 5'-CCCTGAAAGCATCACAATTCTAAA-3' | 17 |
| 2190 forward | 5'-CAACGCGTAGAAGAACGATCTAAA-3' | 18 |
| 2190 reverse | 5'-CCTCCAATTGAGCTTTTTGGTT-3' | 19 |
| SZIC forward | 5'-CGCATGCGGGTAGATTATGTAG-3' | 2 |
| SZIC reverse | 5'-TCCCACGAGAAGGTCGAGAA-3' | 3 |
| eqbE2 probe (FAM) | 5'-ATTGTTACTATGGCTGAAGGT-3' | 20 |
| 2190 probe (VIC) | 5'-AAGCCAAGGAAGCCACT-3' | 21 |
| SZIC probe (NED) | 5'-AGAGACATCCAGGTCAA-3' | 4 |

Figure 1:
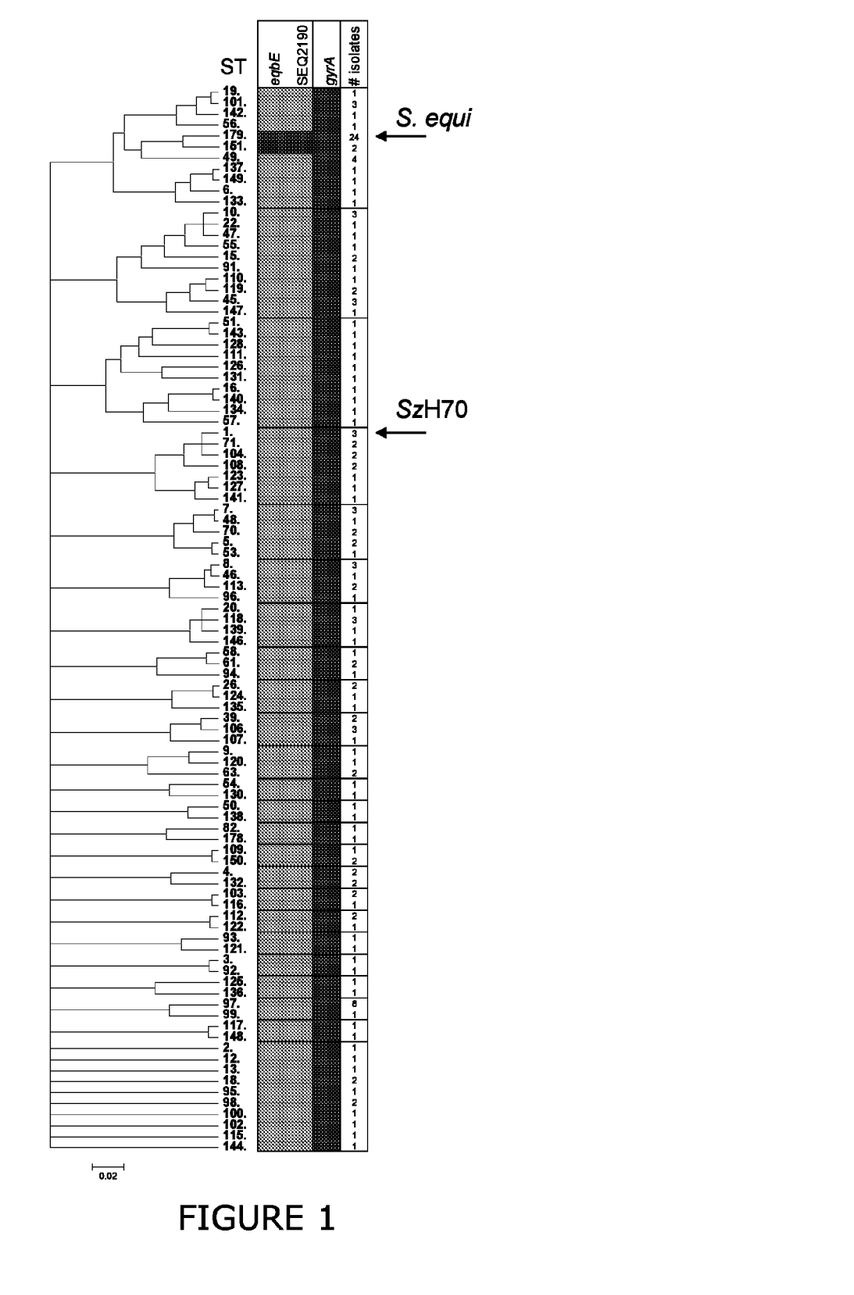
FIG. 1 provides a ClonalFrame analysis of MLST alleles of 26 *S. equi* and 140 *S. zooepidemicus* isolates (as listed in Table 3) and its relationship with the prevalence of eqbE, SEQ2190 and gyrA between the Se4047 and SzH70 genomes. Genes examined were eqbE (within the equibactin locus), SEQ2190 and gyrA. The number of isolates representing each ST is indicated. STs where all isolates contained the gene or possessed functional activity are shown in black. STs where all isolates lacked the gene or functionality are shown in grey. The position of *S. equi* isolates and SzH70 are indicated.

The presence of eqbE and SEQ2190 in a diverse library of 140 *S. zooepidemicus* isolates (Holden et al., 2009 and Table 3) was also determined by PCR with primers ZM435 and ZM436 and 2190A and 2190B (FIG. 1).

TABLE 3

Identity of *S. equi* and *S. zooepidemicus* isolates studied

| Species | ST | Strain ID | Disease/Source | Animal | Year |
|---|---|---|---|---|---|
| Sz | 19 | B27 3726.1 | Uterine infection/abortion | Horse | 2007 |
| Sz | 101 | 3604 | Uterine infection/abortion | Horse | 2006 |
| Sz | 101 | B24 2382 | Uterine infection/abortion | Horse | 2004 |
| Sz | 101 | B24 4996 | Uterine infection/abortion | Horse | 2004 |
| Sz | 142 | 3727 | Uterine infection/abortion | Horse | 2007 |
| Sz | 56 | B23 3322 | Uterine infection/abortion | Horse | 2003 |
| Se | 179 | 3154 | Strangles | Horse | 2004 |
| Se | 179 | 8229 | Strangles | Dog | 2004 |
| Se | 179 | B23 7325 | Strangles | Horse | 2003 |
| Se | 179 | 4047 | Strangles | Horse | 1990 |
| Se | 179 | SA | Strangles | Horse | 1999 |
| Se | 179 | 303 | Strangles | Horse | 1999 |
| Se | 179 | 7060 | Strangles | Horse | 2003 |
| Se | 179 | 1931 | Strangles | Horse | 2004 |
| Se | 179 | 1351 | Strangles | Horse | 2004 |
| Se | 179 | 1350 | Strangles | Horse | 2003 |
| Se | 179 | 7344 | Strangles | Horse | 2003 |
| Se | 179 | 7140 | Strangles | Horse | 2003 |
| Se | 179 | 7171 | Strangles | Horse | 2003 |
| Se | 179 | 7364 | Strangles | Horse | 2003 |
| Se | 179 | 7326 | Strangles | Horse | 2003 |
| Se | 179 | 3155 | Strangles | Horse | 2004 |
| Se | 179 | 3156 | Strangles | Horse | 2004 |
| Se | 179 | 181063 | Strangles | Horse | 1999 |
| Se | 179 | JKS 044 | Strangles carrier | Horse | 2006 |
| Se | 179 | JKS 043 | Strangles | Horse | 2006 |
| Se | 179 | JKS 063 | Strangles | Horse | 2006 |
| Se | 179 | JKS 225 | Strangles | Horse | 2006 |
| Se | 179 | CF32 | Strangles | Horse | 1981 |
| Se | 179 | JKS 559 | Strangles | Horse | 2006 |
| Se | 151 | 7329 | Strangles | Horse | 2006 |
| Se | 151 | Mo | Strangles brain abscess | Horse | 2008 |
| Sz | 49 | B25 4861.1 | Wound infection | Horse | 2005 |
| Sz | 49 | B23 6378 | Uterine infection/abortion | Horse | 2003 |
| Sz | 49 | B27 1175.2 | Uterine infection/abortion | Horse | 2007 |
| Sz | 49 | B26 8276 | Upper respiratory | Horse | 2006 |
| Sz | 137 | 628 | Uterine infection/abortion | Horse | 2007 |
| Sz | 149 | 6619 | Uterine infection/abortion | Horse | 2003 |
| Sz | 6 | S13 | Skin swab | Dog | 2002 |
| Sz | 133 | 2258 | Foot swab | Horse | 2007 |
| Sz | 10 | BHS 32 | Lower respiratory | Dog | 2001 |
| Sz | 10 | BHS 41 | Lower respiratory | Dog | 2001 |
| Sz | 10 | B26 6443 | Wound infection | Horse | 2006 |
| Sz | 22 | BHS 53 | Lower respiratory | Dog | 2001 |
| Sz | 47 | BHS 28 | Lower respiratory | Dog | 2001 |
| Sz | 55 | B23 7163 | Uterine infection/abortion | Horse | 2003 |
| Sz | 15 | B23 6907 | Uterine infection/abortion | Horse | 2003 |
| Sz | 15 | B27 2806.2 | Uterine infection/abortion | Horse | 2007 |
| Sz | 91 | BHS 37 | Lower respiratory | Dog | 2001 |
| Sz | 110 | 4847 | Upper respiratory | Horse | 1996 |
| Sz | 119 | 4904 | Upper respiratory | Horse | 1996 |
| Sz | 119 | 5382 | Upper respiratory | Horse | 1996 |
| Sz | 45 | 605851 | Upper respiratory | Horse | 1996 |
| Sz | 45 | 5845 | Upper respiratory | Horse | 1996 |
| Sz | 45 | D56 | Lower respiratory | Horse | 2000 |
| Sz | 147 | 6875 | Uterine infection/abortion | Horse | 2006 |
| Sz | 51 | B23 6074 | Uterine infection/abortion | Horse | 2003 |
| Sz | 143 | 3512 | Uterine infection/abortion | Horse | 2007 |
| Sz | 128 | 8718.2 | Uterine infection/abortion | Horse | 2006 |
| Sz | 111 | 5831 | Upper respiratory | Horse | 1996 |
| Sz | 126 | 5079 | Uterine infection/abortion | Horse | 2006 |
| Sz | 131 | 3543 | Foot swab | Horse | 2006 |
| Sz | 16 | B24 7132 | Upper respiratory | Horse | 2004 |
| Sz | 140 | B27 3530.1 | Wound infection | Horse | 2007 |
| Sz | 134 | 2567.1 | Udder swab | Horse | 2007 |
| Sz | 57 | JKS 115 | Upper respiratory | Horse | 2006 |
| Sz | 1 | H70 | Upper respiratory | Horse | 2000 |
| Sz | 1 | B27 7271 | Uterine infection/abortion | Horse | 2003 |
| Sz | 1 | B27 0479 | Uterine infection/abortion | Horse | 2007 |
| Sz | 71 | 60 5632 | Upper respiratory | Horse | 1996 |
| Sz | 71 | 60 5013 | Upper respiratory | Horse | 1996 |
| Sz | 104 | 8278 | Upper respiratory | Horse | 2006 |
| Sz | 104 | 8275 | Upper respiratory | Horse | 2006 |
| Sz | 108 | 5938 | Upper respiratory | Horse | 1996 |
| Sz | 108 | 4853 | Upper respiratory | Horse | 1996 |
| Sz | 123 | BHS 5 | Lower respiratory | Dog | 2001 |
| Sz | 127 | 6360 | Wound infection | Horse | 2006 |
| Sz | 141 | 482 | Uterine infection/abortion | Horse | 2007 |
| Sz | 7 | B26 8900 | Wound infection | Horse | 2006 |
| Sz | 7 | B27 1185 | Uterine infection/abortion | Horse | 2007 |
| Sz | 7 | 60 2333 | Upper respiratory | Horse | 1996 |
| Sz | 48 | B25 4433 | Lymph node abscess | Horse | 2005 |
| Sz | 70 | B26 8310 | Upper respiratory | Horse | 2006 |
| Sz | 70 | B26 8277 | Upper respiratory | Horse | 2006 |
| Sz | 5 | B24 7159 | Lymph node abscess | Horse | 2004 |
| Sz | 5 | B24 7043 | Lymph node abscess | Horse | 2004 |
| Sz | 53 | B24 7102.2 | Lymph node abscess | Horse | 2004 |
| Sz | 8 | H8 | Lower respiratory | Horse | 2000 |
| Sz | 8 | D40 | Lower respiratory | Horse | 2000 |
| Sz | 8 | D2a | Lower respiratory | Horse | 2000 |
| Sz | 46 | B25 0061 | Lymph node abscess | Horse | 2005 |
| Sz | 113 | 4885 | Upper respiratory | Horse | 1996 |
| Sz | 113 | 5617 | Upper respiratory | Horse | 1996 |
| Sz | 96 | B25 4763 | Lymph node abscess | Horse | 2005 |
| Sz | 20 | B25 4042.1 | NA | Horse | 2005 |
| Sz | 118 | 3050 | Nasal fluid | Horse | 2007 |
| Sz | 118 | 4901 | Upper respiratory | Horse | 1996 |
| Sz | 118 | 2329 | Upper respiratory | Horse | 1996 |
| Sz | 139 | 972395 | Upper respiratory | Horse | 1997 |
| Sz | 146 | 8250 | Wound infection | Horse | 2006 |
| Sz | 58 | B26 Tansey | Nephritis | Horse | 2006 |
| Sz | 61 | B26 8269.1 | Wound infection | Horse | 2006 |
| Sz | 61 | B26 0225 | Uterine infection/abortion | Horse | 2006 |
| Sz | 94 | B23 6170 | Uterine infection/abortion | Horse | 2003 |
| Sz | 26 | B27 2596 | Uterine infection/abortion | Horse | 2007 |
| Sz | 26 | B26 6993 | Uterine infection/abortion | Horse | 2006 |
| Sz | 124 | 5808 | Wound infection | Horse | 2003 |
| Sz | 135 | 2265 | Intra-abdomen pus | Horse | 2007 |
| Sz | 39 | B26 6334 | Wound infection | Horse | 2006 |
| Sz | 39 | JKS 241 | Upper respiratory | Horse | 2007 |
| Sz | 106 | 605849 | Upper respiratory | Horse | 1996 |
| Sz | 106 | 5936 | Upper respiratory | Horse | 1996 |
| Sz | 106 | 8306 | Upper respiratory | Horse | 2006 |
| Sz | 107 | 8307 | Upper respiratory | Horse | 2006 |
| Sz | 9 | H54 | Upper respiratory | Horse | 2000 |
| Sz | 120 | 4897 | Upper respiratory | Horse | 1996 |
| Sz | 63 | B26 2253 | Uterine infection/abortion | Horse | 2006 |
| Sz | 63 | B26 3540 | Foot swab | Horse | 2006 |
| Sz | 54 | B24 7155 | Upper respiratory | Horse | 2004 |
| Sz | 130 | 7101 | Wound infection | Horse | 2006 |
| Sz | 50 | B25 5405 | Lymph node abscess | Horse | 2005 |
| Sz | 138 | 917 | Uterine infection/abortion | Horse | 2007 |
| Sz | 82 | B26 6458 | Uterine infection/abortion | Horse | 2006 |
| Sz | 178 | 2958 | Uterine infection/abortion | Horse | 2007 |
| Sz | 109 | 5820 | Upper respiratory | Horse | 1996 |
| Sz | 150 | 8311 | Upper respiratory | Horse | 2006 |
| Sz | 150 | 8308 | Upper respiratory | Horse | 2006 |
| Sz | 4 | B27 4388 | Uterine infection/abortion | Horse | 2007 |
| Sz | 4 | B24 4389 | Uterine infection/abortion | Horse | 2004 |
| Sz | 132 | 2853 | Lymph node abscess | Horse | 2007 |
| Sz | 132 | 1913 | Uterine infection/abortion | Horse | 2007 |
| Sz | 103 | 8300 | Upper respiratory | Horse | 2006 |
| Sz | 103 | 8297 | Upper respiratory | Horse | 2006 |
| Sz | 116 | 8293 | Upper respiratory | Horse | 1996 |
| Sz | 112 | 4866 | Upper respiratory | Horse | 1996 |
| Sz | 112 | 5951 | Upper respiratory | Horse | 1996 |
| Sz | 122 | 4871 | Upper respiratory | Horse | 1996 |
| Sz | 93 | B23 7166 | Uterine infection/abortion | Horse | 2003 |
| Sz | 121 | 5185 | Upper respiratory | Horse | 2006 |
| Sz | 3 | D33 | Lower respiratory | Horse | 2000 |
| Sz | 92 | B23 4314B | NA | Horse | 2003 |
| Sz | 125 | 7157 | Upper respiratory | Horse | 2004 |
| Sz | 136 | 3101 | Uterine infection/abortion | Horse | 2007 |

TABLE 3-continued

Identity of S. equi and S. zooepidemicus isolates studied

| Species | ST | Strain ID | Disease/Source | Animal | Year |
|---|---|---|---|---|---|
| Sz | 97 | B26 5081.1 | Uterine infection/abortion | Horse | 2006 |
| Sz | 97 | B26 8570 | Uterine infection/abortion | Horse | 2006 |
| Sz | 97 | B26 8571 | Uterine infection/abortion | Horse | 2006 |
| Sz | 97 | B27 2742.2 | Uterine infection/abortion | Horse | 2007 |
| Sz | 97 | B27 7714 | Lymph node abscess | Horse | 2007 |
| Sz | 97 | B27 0624.2 | Uterine infection/abortion | Horse | 2007 |
| Sz | 97 | B27 0624.1 | Uterine infection/abortion | Horse | 2007 |
| Sz | 97 | B26 8575 | Uterine infection/abortion | Horse | 2006 |
| Sz | 99 | B27 0739 | Uterine infection/abortion | Horse | 2007 |
| Sz | 117 | 5623 | Lower respiratory | Horse | 1996 |
| Sz | 148 | 4875 | Lower respiratory | Horse | 1996 |
| Sz | 2 | D14a | Lower respiratory | Horse | 2000 |
| Sz | 12 | B25 0590 | Wound infection | Horse | 2005 |
| Sz | 13 | B26 0863 | Uterine infection/abortion | Horse | 2006 |
| Sz | 18 | 1770 | Fatal haemorrhagic pneumoniae | Dog | 2008 |
| Sz | 18 | 1727 | Fatal haemorrhagic pneumoniae | Dog | 2008 |
| Sz | 95 | B24 7156 | Upper respiratory | Horse | 2004 |
| Sz | 98 | B26 8337 | Keratitis | Horse | 2006 |
| Sz | 98 | B27 2247 | Uterine infection/abortion | Horse | 2007 |
| Sz | 100 | B26 3593 | Keratitis | Horse | 2006 |
| Sz | 102 | 8299 | Upper respiratory | Horse | 2006 |
| Sz | 115 | 4893 | Upper respiratory | Horse | 1996 |
| Sz | 144 | 2410 | Upper respiratory | Horse | 1997 |

NA = Information not available

Construction of pGHost9ΔSZO07770

Two approximately 500 bp fragments of the SZO07770 pseudogene were PCR amplified from SzH70 using primers Ec07770Fwd1 with Ec07770Rev1a and Ec07770Fwd2 with Ec07770Rev2 (Table 2). PCR products were digested with EcoR1 and Age1, and Pvu1 and Sal1, respectively and ligated into EcoR1 and Sal1 cut pGHost9 to generate pGHost9ΔSZO07770, which was sequenced using primers 5' pGhost9 and 3' pGhost9 (Table 2).

Design and Generation of the Sz07770c Internal Control Strain

A 100 bp sequence of DNA was designed, which had no significant homology with any nucleotide sequences on the NCBI database. Restriction sites for PvuI and AgeI were engineered to the 5' and 3' end of the DNA fragment, respectively and the resultant artificial DNA sequence, SZIC, was produced using the Gene Oracle gene synthesis service. The synthesised SZIC DNA was digested with PvuI and AgeI restriction enzymes and sub-cloned into pGHost9ΔSZO07770 digested with the same restriction enzymes such that the resultant plasmid, pGHost9SZIC, contained SZIC flanked by approximately 500 bp SZO077770 gene fragments. The pGHost9SZIC plasmid was transformed into electrocompetent SzH70. Integration of the construct, insertion of the SZIC sequence into the chromosomal copy of the SZO077770 gene and excision of the pGHost9 plasmid was achieved by allelic replacement mutagenesis as described previously for constructing a ΔprtM mutant (Hamilton et al., 2006). The fidelity of SZIC was confirmed by PCR and sequencing across the SZO07770 insertion site.

To enable simple transfer of the triplex assay to different laboratories the Sz07770c strain, a genetically modified category II pathogen, was grown to an optical density of $0.3_{600nm}$ in Todd Hewitt Broth and heat killed at 95° C. for 30 minutes. No colonies of Sz07770c were obtained when 100 µl of this culture was incubated overnight at 37° C. and 5% $CO_2$ on COBA streptococcal selective agar. The killed culture was diluted to obtain a bacterial density equivalent to 80,000 colony-forming units (cfu)/ml in PBS and stored at −20° C. prior to use.

DNA Extraction 1 ml of clinical and limit of detection samples were spiked with 25 µl of killed diluted Sz07770c, containing bacteria equivalent to 2000 cfu in the original live culture. DNA was extracted using the GenElute kit (Sigma) according to the manufacturer's instructions for isolating DNA from streptococci and eluted in 200 µl $ddH_2O$.

Development and Validation of Triplex qPCR Assay

Compatible primers and minor groove binder (MGB) probes were designed against eqbE, SEQ2190 and SZIC (Table 2). Reaction conditions were optimised for a fast cycling assay using an ABI StepOne Plus instrument with KAPA Fast probe mix (Kapa Biosystems), with a 50:50 master-mix to DNA sample mixture (for one reaction: 10 µl KAPA Fast probe mix, 0.09 µl 100 mM eqbE2 forward, 0.09 µl 100 mM eqbE2 reverse, 0.09 µl 100 mM 2190 forward, 0.09 µl 100 mM 2190 reverse, 0.04 µl 100 mM SZIC forward and 0.04 µl 100 mM SZIC reverse, and 0.03 µl of eqbE2 probe, 2190 probe and SZIC probe and 10 µl DNA). Cycling conditions were 3 minutes activation at 95° C. followed by 40 cycles of 95° C. for 3 seconds and 60° C. for 10 seconds. All qPCR experiments were performed in triplicate.

Validation of Triplex qPCR Assay Using Clinical Samples and Comparison to the Current eqbE Singlex qPCR Assay Ninety-five clinical samples of >2 ml in volume were received by the Animal Health Trust diagnostic laboratories for detection of S. equi via the eqbE singlex qPCR assay. Two 1 ml aliquots of the original clinical sample were removed and blinded. 25 µl of heat-killed Sz07770c was added to one aliquot and both aliquots were then centrifuged at 16,100×g and DNA isolated separately from the pellets using the GenElute kit (Sigma) according to the manufacturer's instructions for isolating DNA from streptococci. The samples containing spiked Sz07770c were assayed using the triplex qPCR assay and the number of copies of eqbE in the DNA isolated from the other aliquot was quantified by qPCR using the eqbE singlex assay by the Animal Health Trust's diagnostic laboratory.

RESULTS

Conservation of eqbE and SEQ2190 Targets

The S. equi-specific eqbE and SEQ2190 targets were identified on comparison of the Se4047 and SzH70 genomes (Heather et al., 2008; Holden et al., 2009). The eqbE and SEQ2190 target sequences were unique to S. equi and had no known homology to non-S. equi sequences on the NCBI database. PCR and sequencing of a 1,063 bp region of eqbE (position 1,229,518 to 1,228,456 of the Se4047 genome) and a 449 bp region of SEQ2190 (position 2,203,349 to 2,203,797 of the Se4047 genome) found that these sequences were identical across all 26 strains of S. equi examined.

Generation of the Sz07770c Strain

PCR and sequencing across the insertion site confirmed that the SZIC sequence had successfully been incorporated into the SZO07770 pseudogene in the Sz07770c strain and that all plasmid DNA had been excised. The Sz07770c strain was sensitive to erythromycin.

Limit of Detection of the Triplex qPCR Assay

Figure 2:
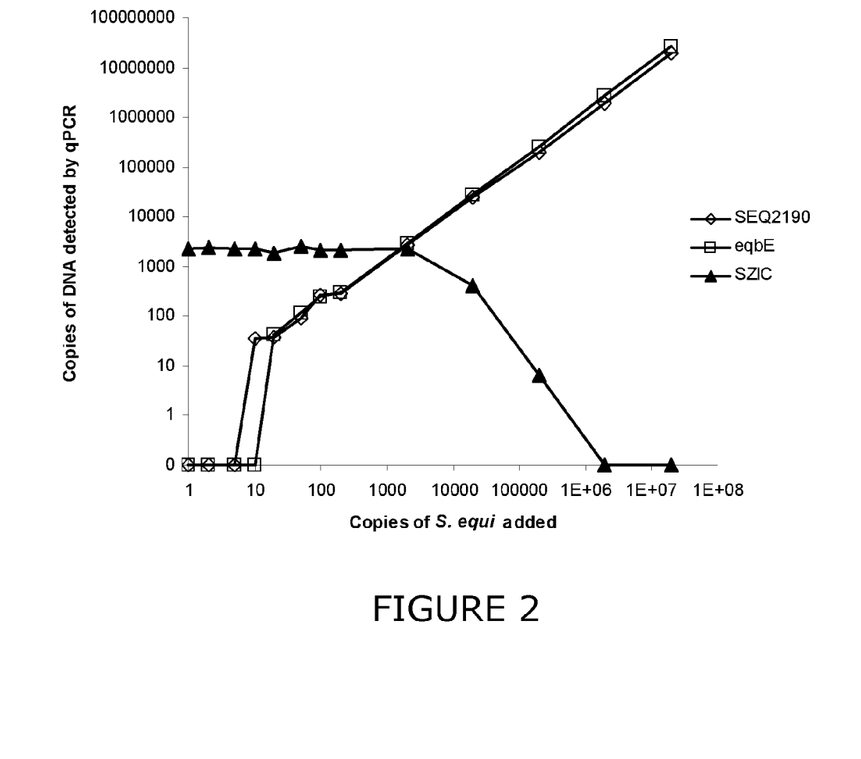
FIG. 2 demonstrates the limit of detection of the eqbE and SEQ2190 qPCR assays in samples spiked with 2,000 copies of SZIC.

The SZIC assay detected approximately 2,000 copies in all reactions where the amount of S. equi DNA was 2,000 copies or less. *S. equi* DNA levels of $2\times10^4$ copies per reaction or higher interfered with the SZIC qPCR assay. The triplex assay had a limit of detection of 20 and 10 copies of *S. equi* DNA via the eqbE and SEQ2190 qPCR assays, respectively (FIG. 2).

Validation of Triplex qPCR Assay Using Clinical Samples and Comparison to the Current eqbE Singlex qPCR Assay Thirteen of 100 clinical samples tested positive for *S. equi* via the eqbE singlex qPCR assay and 87 tested negative. Twelve of the singlex-positive and two singlex-negative sample tested positive for *S. equi* using the triplex assay giving an overall sensitivity of 93.3% and specificity of 97.7%.

DISCUSSION

Quantitative PCR permits the rapid and sensitive detection of target DNA sequences and offers significant advantages over traditional culture tests, which are often confounded by the presence of *S. zooepidemicus*. However, particular care is required to ensure both the specificity and conservation of selected target sequences. The sequence of the 5' region of SeM targeted by the first *S. equi* PCR tests has been shown to be highly diverse and is deleted in some strains recovered from persistently infected carriers. The superantigen-encoding genes seeH, seeI, seeL and seeM are encoded on the prophage φSeq4 and φSeq3 and may excise and/or transfer to *S. zooepidemicus*. The production of four superantigens confers a certain level of functional redundancy (Paillot et al., 2010) and *S. zooepidemicus* multilocus sequence types ST-106, ST-118 and ST-120 were qPCR positive for seeL and seeM (Holden et al., 2009), suggesting that the use of these targets may lead to the identification of false-positive results due to the presence of certain *S. zooepidemicus* strains. The gene encoding the factor H-binding protein Se18.9 is also present in ST-57 strains of *S. zooepidemicus* (Holden et al., 2009), suggesting that qPCRs targeting this sequence may also lead to false-positive results.

We exploited emerging genome sequencing data and our extensive global collections of *S. equi* and *S. zooepidemicus* to select two conserved *S. equi*-specific targets that are located in separate regions of the Se4047 genome. The eqbE gene forms part of the equibactin locus, which is believed to encode a non-ribosomal peptide synthesis system that enhances the ability of *S. equi* to acquire iron (Heather et al., 2008). The acquisition of this locus has been suggested to represent the speciation event of *S. equi* and is proposed to be important for the rapid development of lymph node abscesses. The equibactin locus is encoded on an integrative conjugative element, ICESe2, which has the potential for horizontal transfer, although this has not yet been demonstrated and the locus appears to be restricted to *S. equi*.

SEQ2190 encodes a putative sortase-processed protein and is present in all strains of *S. equi* screened for this target. A partial homologue of SEQ2190, SZO18970, lacking the 5' region targeted by the triplex assay is present in SzH70 (Holden et al., 2009). However, none of the 140 diverse strains of *S. zooepidemicus* examined tested qPCR positive for SEQ2190 and the target region was absolutely conserved in the 26 strains of *S. equi* strains tested.

Targeting both eqbE and SEQ2190 significantly reduces the chance of infrequent, yet important situations occurring where the diagnostic target is lost in a strain, resulting in the failure of the test and subsequent clonal expansion of the modified strain as occurred with *C. trachomatis* in Sweden (Seth-Smith et al., 2009).

The novel internal control strain, Sz07770c, which serves as a DNA extraction and assay control ensures that all clinical samples should generate a qPCR result. High levels of *S. equi* DNA ($>2\times10^4$ copies) out-compete the SZIC assay and generate eqbE, SEQ2190 positive; SZIC negative results. Clinical samples containing moderate to low quantities of *S. equi* (between $2\times10^4$ and 20 copies) yield eqbE, SEQ2190 and SZIC positive results. Samples containing <20 copies of *S. equi* DNA yield eqbE, SEQ2190 negative; SZIC positive results, thereby ruling out the possibility that *S. equi* could have been present in the is sample, but was missed due to a DNA extraction failure. These results permit robust quality control of the data generated and will ensure that a reliable diagnosis is provided to submitting veterinarians.

The inhibition of SZIC amplification when higher concentrations of *S. equi* DNA are present does not invalidate the assay because the purpose of SZIC is to confirm that the extraction and qPCR were successful, and high levels of *S. equi* confirms that these procedures have worked. High levels of *Bacillus anthracis*, *Francisella tularensis*, and *Yersinia pestis* were noted to inhibit the detection of the *Bacillus thuringensis* internal control in a multiplex qPCR assay (Janse et al., 2010). However, it is highly important that the amplification of internal control sequences do not inhibit the amplification of pathogen target DNA, particularly when low concentrations of pathogen DNA are present. The strangles triplex qPCR assay was optimised to ensure that amplification of low concentrations of *S. equi* DNA (20 copies) was not inhibited by the presence of SZIC and that the *S. equi* qPCR copy numbers obtained from clinical samples using the triplex assay were comparable to those obtained using an assay based only on eqbE. The triplex assay has a qPCR run time of 30 minutes and a larger volume of DNA extracted from the submitted clinical sample is added, maximising sensitivity.

CONCLUSIONS

The use of sensitive qPCR assays will improve the identification and treatment of horses persistently infected with *S. equi*, which often intermittently shed low levels of *S. equi* that can easily be missed by traditional culture and PCR assays. The strangles triplex assay of the invention provides a rapid, sensitive and robust method for the detection of *S. equi* infection.

REFERENCES

Anzai, T. et al., 2005. Am J Vet Res 66, 2167-2171.
Bannister, M. F. et al., 1985. J Clin Microbiol 21, 524-526.
Baverud, V. et al., 2007. Vet Microbiol 124, 219-229.
Chanter, N. et al., 2000. Microbiology 146 (Pt 6), 1361-1369.
Galan, J. E., Timoney, J. F., 1988. J Clin Microbiol 26, 1142-1146.
Hamilton, A. et al. 2006. Infection and Immunity 74, 6907-6919.
Heather, Z. et al., 2008. Mol Microbiol 70, 1274-1292.
Holden, M. T. et al., 2009. PLoS Pathog 5, e1000346.
Janse, I. et al., 2010. BMC Microbiol 10, 314.
Kelly, C. et al., 2006. J Clin Microbiol 44, 480-486.
Newton, J. R. et al., 2000. Equine Vet J 32, 515-526.
Newton, J. R. et al., 1997. Vet Rec 140, 84-90.
Paillot, R. et al., 2010. Infect Immun 78, 1728-1739.
Seth-Smith, H. M. et al., 2009. BMC Genomics 10, 239.
Timoney, J. F., Artiushin, S. C., 1997. Vet Rec 141, 446-447.

The invention claimed is:

1. A method for detecting the presence or absence of *Streptococcus equi* in a biological sample, the method comprising the steps of:
   (a) adding a control bacterial strain to the biological sample, wherein the sample is obtained from an animal subject, and wherein the genome of the control bacterial strain contains a target sequence region comprising the nucleotide sequence of: 5'-CCGTGTATTACGCAT-GCGGGTAGATTATGTAGGTAGAGACATCCAG-GTCAAGTTCTCGAC CTTCTCGTGGGAGGT-GAACCAG-3' (SEQ ID NO: 1);
   (b) assessing the sample for the presence or absence of the *Streptococcus equi* SEQ 2190 and/or eqbE gene, wherein detection of the *Streptococcus equi* SEQ 2190 and/or eqbE gene is indicative of a positive identification for *Streptococcus equi* in the biological sample; and
   (c) assessing the sample for the presence of the target sequence region within the control bacterial strain, wherein detection of the target sequence region within the control bacterial strain is indicative of an accurate result for step (b).

2. The method according to claim 1, wherein the control bacterial strain is a *Streptococcus zooepidemicus* strain.

3. The method according to claim 2, wherein the *Streptococcus zooepidemicus* strain is *Streptococcus zooepidemicus* H70.

4. The method according to claim 1, wherein the sample is obtained from an equine.

5. The method according to claim 1, wherein the biological sample comprises a nasal swab or wash, pus from an abscess or lavage of the guttural pouch.

6. The method according to claim 1, wherein the assessing step (b) comprises detecting the *Streptococcus equi* (eqbE) gene.

7. The method according to claim 6, wherein detecting the eqbE gene comprises using the primers and probes of SEQ ID NOS: 16, 17 and 20.

8. The method according to claim 1, wherein the assessing step (b) comprises detecting the *Streptococcus equi* eqbE and SEQ 2190 genes.

9. The method according to claim 1, wherein the assessing step (b) comprises detecting the SEQ 2190 gene.

10. The method according to claim 9, wherein detecting the SEQ 2190 gene comprises using the primers and probes of SEQ ID NOS: 18, 19 and 21.

11. The method according to claim 1, wherein the sample is obtained from a horse, a donkey or a mule.

* * * * *